United States Patent [19]
Pop

[11] Patent Number: 5,904,678
[45] Date of Patent: *May 18, 1999

[54] MULTIZONE, MULTIPASS PHOTOREFRACTIVE KERATECTOMY

[75] Inventor: Mihai Pop, Quebec, Canada

[73] Assignee: LaserSight Technologies, Inc., Orlando, Fla.

[*] Notice: This patent issued on a continued prosecution application filed under 37 CFR 1.53(d), and is subject to the twenty year patent term provisions of 35 U.S.C. 154(a)(2).

[21] Appl. No.: 08/664,726

[22] Filed: Jun. 17, 1996

Related U.S. Application Data

[60] Provisional application No. 60/000,304, Jun. 19, 1995.

[51] Int. Cl.$^6$ .................................................. A61B 17/36
[52] U.S. Cl. .................................................. 606/5; 606/4
[58] Field of Search ................................ 606/4, 5, 6, 10, 606/11, 12

[56] References Cited

U.S. PATENT DOCUMENTS

| | | |
|---|---|---|
| 3,697,889 | 10/1972 | Dewey, Jr. . |
| 3,743,965 | 7/1973 | Offner . |
| 3,848,104 | 11/1974 | Locke . |

(List continued on next page.)

FOREIGN PATENT DOCUMENTS

| | | |
|---|---|---|
| 0 151869 A1 | 8/1985 | European Pat. Off. . |
| 0368512A2 | 5/1990 | European Pat. Off. . |
| 0418890A3 | 3/1991 | European Pat. Off. . |

OTHER PUBLICATIONS

Qiushi Ren, Raymond P. Galitis, Keith P. Thompson, & J.T. Lin, "Ablation of the Cornea and Synthetic Polymers Using a UV (213 nm) Solid State Laser", IEEE Journal of Quatum Electronics, Dec. 1990, pp. 2284–2288.

Conference on Lasers and Electro–Optics, Optical Society of America, May 1990, pp. 28–30.

G.P.A. Malcom, M.A. Persaud, & A.I. Ferguson, "Resonant Frequency Quadrupling of a Mode—Locked Diode—Pumped Nd: YLF Laser", Optics Letters, Jul. 1991, pp. 983–985.

J.T. Lin, J.L. Montgomery, "Temperature—Tuned Noncritically Phase—Matched Frequency Conversion in $LiB_3O_5$ Crystal", Optics Communications, Dec. 1990, pp. 159–165.

A.A. Babin, F.I. Fel'dshtein, & I.V. Yakovlev, "Generation of the Fifth Harmonic of Yttrium Orthoaluminate: $Nd^{3+}$ Laser Radiation in KDP at Room Temperatures", Soviet Technical Physics Letters, Jun. 1990, pp. 417–418.

V.D. Volosov & E.V. Nilov, "Effect of the Spatial Structure of a Laser Beam on the Generation of the Second Harmonic in ADP and KDP Crystals", UDC, Nov. 1965, pp. 715–719.

A.G. Arutyunyan, G.G. Gurzadyan, & R.K. Ispiryan, "Generation of the Fifth Harmonic of Picosecond Yttrium Aluminate Laser Radiation", Soviet Journal Quantum Electron, Dec. 1989, pp. 1602–1603.

(List continued on next page.)

Primary Examiner—Lee Cohen
Assistant Examiner—Sonya Harris-Ogugua
Attorney, Agent, or Firm—Farkas & Manelli PLLC; William H. Bollman

[57] ABSTRACT

A multizone, multipass photorefractive keratectomy (MP-PRK) technique to treat 315 eyes with the 193-nm VISX 20/20 excimer laser. The procedure includes making multipass ablations that increase in ablative depth to create as step-wise ablation of the corneal to the predetermined dioptric correction. It also includes making multizone ablations that create of variable widths that result in a predetermined ablative depth with smooth transition edges. A combination of multizone, multipass ablations are used to treat astigmatism. New algorithms effectively treat the full range of myopia, including low myopic eyes (–1 to –6 D), moderately myopic eyes (–6 to –10 D); and highly myopic eyes (–10 to –27 D).

16 Claims, 3 Drawing Sheets

U.S. PATENT DOCUMENTS

| | | |
|---|---|---|
| 3,938,058 | 2/1976 | Yamamoto . |
| 3,982,541 | 9/1976 | L'Esperance, Jr. . |
| 3,983,507 | 9/1976 | Tang et al. . |
| 4,180,751 | 12/1979 | Ammann . |
| 4,349,907 | 9/1982 | Campillo et al. . |
| 4,386,428 | 5/1983 | Baer . |
| 4,477,159 | 10/1984 | Mizuno et al. . |
| 4,520,816 | 6/1985 | Schachar et al. . |
| 4,538,608 | 9/1985 | L'Esperance, Jr. . |
| 4,573,467 | 3/1986 | Rich et al. . |
| 4,580,559 | 4/1986 | L'Esperance, Jr. . |
| 4,633,866 | 1/1987 | Peyman et al. . |
| 4,665,913 | 5/1987 | L'Esperance, Jr. ........................ 606/5 |
| 4,669,466 | 6/1987 | L 'Esperance, Jr. . |
| 4,718,418 | 1/1988 | L 'Esperance, Jr. . |
| 4,721,379 | 1/1988 | L 'Esperance, Jr. . |
| 4,729,372 | 3/1988 | L 'Esperance, Jr. . |
| 4,729,373 | 3/1988 | Peyman . |
| 4,732,148 | 3/1988 | L'Esperance, Jr. ........................ 606/5 |
| 4,764,930 | 8/1988 | Bille et al. . |
| 4,773,414 | 9/1988 | L'Esperance, Jr. ........................ 606/5 |
| 4,784,135 | 11/1988 | Blum et al. . |
| 4,798,204 | 1/1989 | L'Esperance, Jr. ........................ 606/5 |
| 4,838,266 | 6/1989 | Koziol et al. . |
| 4,840,175 | 6/1989 | Peyman . |
| 4,848,340 | 7/1989 | Bille et al. . |
| 4,856,513 | 8/1989 | Muller . |
| 4,862,886 | 9/1989 | Clarke et al. . |
| 4,903,695 | 2/1990 | Warner et al. . |
| 4,911,711 | 3/1990 | Telfair et al. . |
| 4,925,523 | 5/1990 | Braren et al. . |
| 4,941,093 | 7/1990 | Marshall et al. . |
| 4,975,918 | 12/1990 | Morton . |
| 4,994,058 | 2/1991 | Raven et al. . |
| 5,019,074 | 5/1991 | Muller . |
| 5,052,004 | 9/1991 | Gratze et al. . |
| 5,061,342 | 10/1991 | Jones ........................................... 606/5 |
| 5,065,046 | 11/1991 | Guyer . |
| 5,074,859 | 12/1991 | Koziol . |
| 5,108,388 | 4/1992 | Trokel . |
| 5,108,412 | 4/1992 | Krumeich et al. ...................... 606/4 X |
| 5,144,630 | 9/1992 | Lin . |
| 5,163,934 | 11/1992 | Munnerlyn ................................ 606/5 |
| 5,163,936 | 11/1992 | Black et al. . |
| 5,182,759 | 1/1993 | Anthon et al. . |
| 5,188,631 | 2/1993 | L 'Esperance, Jr. . |
| 5,196,006 | 3/1993 | Klopotek et al. . |
| 5,207,668 | 5/1993 | L 'Esperance, Jr. . |
| 5,217,452 | 6/1993 | O'Donnell . |
| 5,219,343 | 6/1993 | L 'Esperance, Jr. . |
| 5,219,344 | 6/1993 | Yoder, Jr. . |
| 5,226,903 | 7/1993 | Mizuno . |
| 5,257,988 | 11/1993 | L 'Esperance, Jr. . |
| 5,263,950 | 11/1993 | L 'Esperance, Jr. . |
| 5,284,477 | 2/1994 | Hanna et al. . |
| 5,312,320 | 5/1994 | L 'Esperance, Jr. . |
| 5,324,281 | 6/1994 | Muller . |
| 5,334,190 | 8/1994 | Seiler . |
| 5,353,262 | 10/1994 | Yakymyshyn et al. . |
| 5,360,424 | 11/1994 | Klopotek . |
| 5,363,388 | 11/1994 | Shi et al. . |
| 5,364,388 | 11/1994 | Koziol . |
| 5,370,641 | 12/1994 | O'Donnell, Jr. . |
| 5,395,356 | 3/1995 | King et al. .................................. 606/4 |
| 5,395,362 | 3/1995 | Sacharoff et al. . |
| 5,405,355 | 4/1995 | Peyman et al. . |
| 5,411,501 | 5/1995 | Klopotek . |
| 5,423,801 | 6/1995 | Marshall et al. . |
| 5,425,727 | 6/1995 | Koziol . |
| 5,425,729 | 6/1995 | Ishida et al. . |
| 5,437,658 | 8/1995 | Muller et al. . |
| 5,442,487 | 8/1995 | Mizuno . |
| 5,445,633 | 8/1995 | Nakamura et al. . |
| 5,461,212 | 10/1995 | Seiler et al. . |
| 5,470,329 | 11/1995 | Sumiya . |
| 5,480,396 | 1/1996 | Simon et al. . |
| 5,505,723 | 4/1996 | Muller . |
| 5,507,741 | 4/1996 | L 'Esperance, Jr. . |
| 5,507,799 | 4/1996 | Sumiya . |
| 5,549,597 | 8/1996 | Shimmick et al. . |
| 5,549,599 | 8/1996 | Sumiya ..................................... 606/10 |
| 5,556,395 | 9/1996 | Shimmick et al. . |
| 5,586,980 | 12/1996 | Kremer et al. .............................. 606/4 |
| 5,599,340 | 2/1997 | Simon et al. . |
| 5,613,965 | 3/1997 | Muller . |
| 5,624,436 | 4/1997 | Nakamura et al. . |
| 5,637,109 | 6/1997 | Sumiya . |
| 5,646,791 | 7/1997 | Glockler . |
| 5,651,784 | 7/1997 | Klopotek . |
| 5,683,379 | 11/1997 | Hohla . |
| 5,711,762 | 1/1998 | Trokel . |
| 5,713,892 | 2/1998 | Shimmick . |
| 5,735,843 | 4/1998 | Trokel . |

OTHER PUBLICATIONS

Shinichi Imai, Toshitaka Yamada, Yasutomo Fujimori & Ken Ishikawa, Third—Harmonic Generation of an Alexandrite Laser in $\beta$–$BaB_2O_4$ , Applied Physics Letters, May 1989, pp. 1206–1208.

Conference on Lasers and Electro–Optics, Optical Society of America, Apr. 1989, p. 390.

MULTIZONE, MULTIPASS PHOTOREFRACTIVE KERATECTOMY

This application is a non-provisional patent application based upon provisional patent application Ser. No. 60/000,304, filed Jun. 19, 1995.

BACKGROUND OF THE INVENTION

This invention relates generally to the use of new excimer laser procedure designed to correct low to high myopia and, in particular, a method of using algorithm-driven lasers to correct vision by performing multipass ablations, multizone ablations or a combination thereof.

Previous studies performed in different centers suggest that standard PRK for low myopia predictable with few complications. Contrastingly, results in myopia higher than −6 D are more unpredictable due to regression of effect often accompanied by scar formation. Because the quality of the ablation is an important factor in the final visual outcome, one of the first attempts to improve post-operative visual acuity was to limit ablation depth by using multizone techniques. However, there is no change in the degree of haze or in regression when using the technique.

To circumvent the amount of correction allowed by some laser software programs. PRK was performed in a series of steps. For example, a two-step procedure or a multi-step PRK was tried with little haze formation. A different approach involves a second ablation, created outside of the initial, standard PRK ablation, produced a transition zone. This procedure resulted in less regression, but the healing process took longer.

Although regression was lessened, results in eyes above −10 D were so discouraging that intrastromal PRK or laser assisted in situ keratomileusis (LASIK) have been suggested instead of superficial PRK in these patients.

SUMMARY OF THE INVENTION

It is believed that the multizone, multipass approach including the new algorithms described herein is an effective, safe alternative to conventional or more aggressive treatments of low, moderate and high myopia. The multizone aspect of the technique limits the depth of the ablation, while the multipass portion smoothes the ablated surface.

The results obtained with these new algorithms are compared to those obtained with other protocols. Three groups of low, moderate, and highly myopic eyes, with or without astigmatism, were analyzed for haze, central islands, pre- and post-operative refractions, best corrected visual acuity (BCVA), uncorrected visual acuity (UCVA), and loss of best corrected visual acuity (LBCVA).

Far less regression is found in patients treated with the multipass technique. The good initial results with MP-PRK technique allows one to perform surgery bilaterally in low myopes, and to treat very high myopes with little or no residual myopia after one procedure.

DESCRIPTION OF THE PREFERRED EMBODIMENT

Materials And Methods

Figure 5:
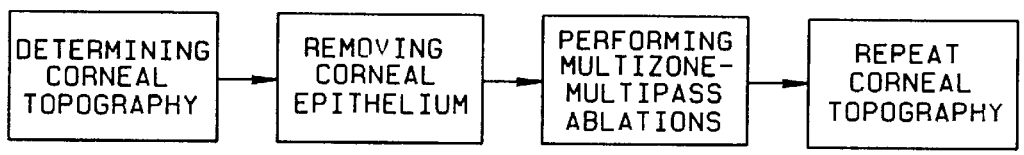
FIG. 5 is a flow chart of the laser surgical procedure of the present invention.

Beginning in November 1993, a new multizone, multipass photorefractive keratectomy technique (MP-PRK) has been performed on 315 eyes by one surgeon using two VISX 20/20 excimer lasers at two locations to correct myopia ranging from sphere values of −1 to −27 D; 185 of these had astigmatism of −0.5 to −4.75 D. The new keratectomy procedure of the present invention is best illustrated in FIG. 5.

All patients were Caucasians, from 19 to 65 years of age, with a mean of 36 years; 137 (43.5%) were male eyes and 178 (56.5%) were female eyes.

Preoperative corneal topography is done three to four days before surgery. At that time a preoperative refraction is also performed. Soft contacts must be removed at least two weeks prior to surgery, and hard or rigid gas permeable lenses must be removed at least three weeks before surgery.

Anesthesia consists of 6 drops of proparacaine hydrochloride (Alcon) and 6 drops of a non-steroidal anti-inflammatory agent ketorolac tromethamine (Acular, Allergan).

After installation of drops, the epithelium is mechanically removed in 20 to 35 seconds with a random 6 to 12 o'clock movement using a blunt Beaver blade. No irrigation is performed, and the eye is not fixated except in rare instances of nystagmus or in the case of a very nervous, mobile patient.

Figure 6A:
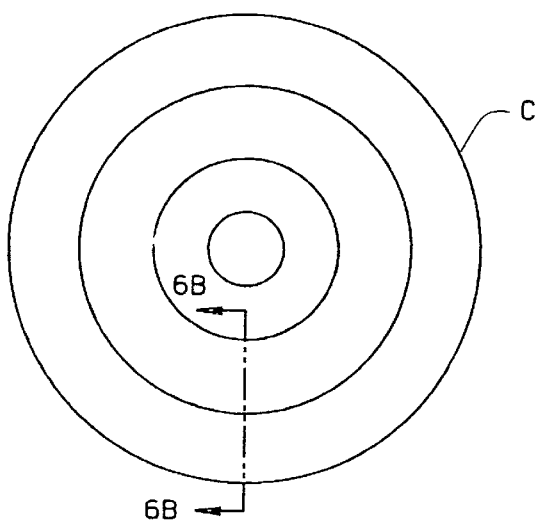
FIG. 6A illustrates multipass laser ablation of the cornea.
Figure 6B:
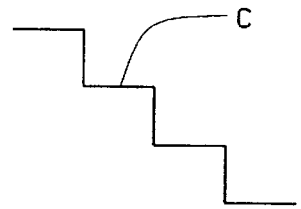
FIG. 6B is a cross-section taken across line 6B—6B of FIG. 6A.

Low (−1.00 D to −6.00 D), moderate (−6 to −10 D), and high (−10.00 D to −27.00 D) myopes all received multizone, multipass treatments. Multipass photorefractive keratectomy was developed in order to try and reduce some of the problems inherent with an eximer laser. As shown in FIGS. 6A and 6B, instead of having one ablation with a single ablative cut, there are multiple ablations of cornea C from an outer circle to an inner circle or zone of decreasing ablative depth. For example, if multipass correction is to be performed to provide correction of approximately 10 diopters in order to correct a vision problem, and it has been precalculated that the depth of ablation must be 100 microns, the surgical laser focal lens, which may function like a mechanical iris, could be widened or narrowed to the diameter required and for each ablative procedure performed, the laser must be adjusted uniformly, outwardly until the depth required has been met and the width for ablation achieved, creating a 10 diopter correction. This procedure, as shown, creates a series of steps (FIG. 6B) rather than one major depression, as performed with a conventional excimer.

Multizone photorefractive keratectomy takes keratectomy one step further because it decreases the depth of ablation rather than attempting to provide a graduated smoothing.

Figure 7A:
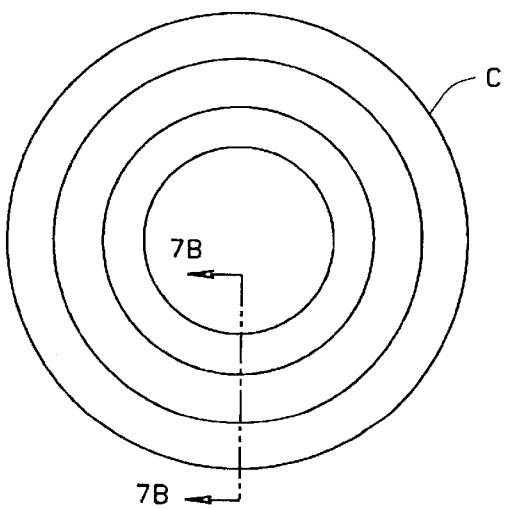
FIG. 7A illustrates multizone laser ablation of the cornea.
Figure 7B:
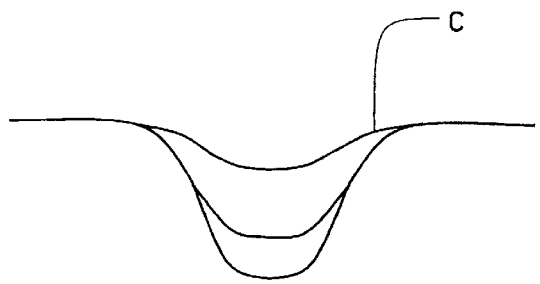
FIG. 7B is a cross section taken across line 7B—7B of FIG. 7A.

Multizone ablation achieves the 10 diopter correction by varying the width to irregular dimensions, as shown in FIGS. 7A and 7B. For example, the first ablative procedure may create a zone 4 mm wide, the second may create a zone 6 mm wide, over the first zone, while the third zone be 7 mm wide over the second zone, resulting in the desired depth of ablation. By performing the ablations in this manner, as shown in FIGS. 7A and 7B, the combination of ablations has smooth drop-off perimeters rather than being stepped, as in multipass, or abruptly cut, as in regular or conventional procedure. Furthermore, through the use of multizone keratectomy, it has been found that the actual depth required to obtain the same dioptric correction may be a lesser percentage of depth than is required through multipass or the conventional laser procedure.

A combination of multizone and multipass ablation to achieve the desired results. Moreover, the ablations are based upon the novel algorithms, as will be explained below. For example, astigmatism is treated with an elliptical ablation combined with multizone, multipass ablations. Each ablative pass lasts from 10 to 20 seconds. As many as seven passes have been used; these are titrated to the patient's refractive error.

There two types of software or algorithms that drive the above described multizone or multipass ablations. First, one laser uses software version 2.7 (revised Feb. 18, 1992) which requires 10 to 15 seconds to program between passes. At the other site, the laser uses software version 4.01 which integrates a pretreatment ablation in the central zone, and requires 45 to 60 seconds to program the next pass.

With version 2.7, patients were treated according to newly devised algorithms: Table 1 shows myopic correction when astigmatism is not present.

TABLE 1

Multipass algorithms in diopters for eyes with astigmatism

| $S_1$ | Pre X 2.5 | 3.5 | 4.0 | 4.5 | 5.0 | 5.5 | 6.0 |
|---|---|---|---|---|---|---|---|
| −1.00 | 1.5 | | | | | | 1 |
| −2.00 | 1.5 | | | | | 1 | 1 |
| −3.00 | 1.5 | | | | | 2 | 1 |
| −4.00 | 1.5 | | | | 2 | 1 | 1 |
| −5.00 | 1.5 | | | | 3 | 1 | 1 |
| −6.00 | 1.5 | | | 3 | 1 | 1 | 1 |
| −7.00 | 1.5 | | | 4 | 1 | 1 | 1 |
| −8.00 | 1.5 | | | 4 | 2 | 1 | 1 |
| −9.00 | 1.5 | | | 4 | 2 | 2 | 1 |
| −10.00 | 1.0 | | | 4 | 2 | 2 | 2 |
| −11.00 | 1.0 | | 4 | 2 | 2 | 2 | 1 |
| −12.00 | 1.0 | | 4 | 3 | 2 | 2 | 1 |
| −13.00 | 1.0 | | 4 | 4 | 2 | 2 | 1 |
| −14.00 | 1.0 | | 4 | 4 | 2 | 2 | 2 |
| −15.00 | 1.0 | | 4 | 4 | 3 | 2 | 2 |
| −16.00 | 1.0 | | 4 | 4 | 4 | 2 | 2 |
| −17.00 | 1.0 | 4 | 4 | 3 | 2 | 2 | 2 |
| −18.00 | 1.0 | 4 | 4 | 4 | 2 | 2 | 2 |
| −19.00 | 1.0 | 4 | 4 | 4 | 3 | 2 | 2 |
| −20.00 | 1.0 | 4 | 4 | 4 | 4 | 2 | 2 |

The intended total spherical correction appears in the first column. The treatment is determined by the numbers appearing on the same line. A pre-treatment at a 2.5 mm diameter of 1 or 1.5 D is done initially depending on the degree of myopia; the rest of the treatment is divided into a number of small corrections between 3.5 to 6.0 mm in diameter.

Table 2 integrates cylindrical correction at 5 mm for astigmatic eyes in which the cylinder is smaller than or equal to the sphere.

TABLE 2

Multipass algorithms in diopters for eyes with astigmatism where the intended sphere correction ($S_i$) is equal or greater than the intended cylinder correction ($C_i$)

| $S_1$ | Pre X 2.5 | 3.5 | 4.0 | 4.5 | 5.0 | 5.5 | 6.0 |
|---|---|---|---|---|---|---|---|
| −1.00 | 1.5 | | | | | | |
| −2.00 | 1.5 | | | | | 1 | 1 |
| −3.00 | 1.5 | | | | | 2 | 1 |
| −4.00 | 1.5 | | | | 2 | 1 | 1 |
| −5.00 | 1.5 | | | | 3 | 1 | 1 |
| −6.00 | 1.5 | | | | 3 | 2 | 1 |
| −7.00 | 1.5 | | | | 4 | 2 | 1 |
| −8.00 | 1.5 | | 3 | 3 | 1 | 1 | |
| −9.00 | 1.5 | | 4 | 2 | 2 | 2 | |
| −10.00 | 1.0 | | 4 | 2 | 2 | 2 | |
| −11.00 | 1.0 | | 4 | 2 | 2 | 2&1 | |
| −12.00 | 1.0 | | 4 | 3 | 2 | 2&1 | |
| −13.00 | 1.0 | | 4 | 4 | 2 | 2&1 | |
| −14.00 | 1.0 | | 4 | 4 | 3 | 2&2 | |
| −15.00 | 1.0 | | 4 | 4 | 3 | 2&2 | |
| −16.00 | 1.0 | | 4 | 4 | 4 | 2&2 | |
| −17.00 | 1.0 | 4 | 4 | 3 | 2 | 2&2 | |
| −18.00 | 1.0 | 4 | 4 | 4 | 2 | 2&2 | |
| −19.00 | 1.0 | 4 | 4 | 4 | 3 | 2&2 | |
| −20.00 | 1.0 | 4 | 4 | 4 | 4 | 2&2 | |

To use this Table, the intended cylindrical correction ($C_i$) is first calculated. If S is the initial sphere value in diopters and C is the initial cylindrical value, then $C_i=C+0.25C+0.50$. The cylinder correction will be performed at a diameter of 5.0 mm. An equal amount of sphere will be corrected at the same time. For every 2.25 D maximum of C; one pass is performed. If, for example, the intended correction is 3 D of cylinder, two passes are performed at 1.50 D. Next, the intended sphere correction ($S_i$) is determined by using the subjective sphere value (S) and the corneal sphere value ($S_c$) corresponding to the subjective value: If $S<-10$ D, then $S_i=S_c$ If $S>-10$ D, then $S_i=(S+S_c)/2$ To calculate the residual sphere correction ($S_r$):

$$S_r=S_i-C_i$$

First, the pretreatment is performed at 2.5 mm, the cylinder plus an equal amount of sphere is corrected at 5 mm, finally the residual amount of sphere is corrected by algorithms given for the residual sphere correction in Table 2.

To correct astigmatic eyes in which the cylinder is greater than the sphere, the amount of intended cylinder ($C_i$) to be corrected is calculated:

$$C_i=C+0.25+0.50$$

To calculate the residual cylinder correction ($C_r$), the intended spherical ($S_i$) correction is subtracted from the intended cylindrical correction:

$$C_r=C_i-S_i$$

The treatment is performed in three stages: first, a pretreatment of 1.5 D at 2.5 mm; next, the residual cylinder correction is performed with a cylindrical ablation of 5 by 4 mm with one pass for every 2 D or less of cylinder value; finally, the sphere with an equal amount of cylinder is corrected with a 6 mm elliptical ablation.

With the version 4.01, Table 1, minus the pre-treatment, is used to correct myopia without astigmatism. To correct myopia with astigmatism, the cylinder will be corrected at an aperture of 6 mm, with $C_i = C$ and the $S_i = S_c$ All eyes received the same regimen post-operatively. In the immediate post-operative period, Acular is given four times daily for 24 hours, then every 12 hours for 48 hours. Ciloxan (Alcon) is given four times daily for 72 hours. Steroids are not used during this period. A soft contact lens (Acuvue, Johnson & Johnson, or NewVues, Ciba Vision) is placed on the operated eye.

Long term post-operative care includes coticosteroids: fluorometholone acetate (Flarex, Alcon) started on the third post-operative day, bid (twice a day) for three months. Artificial tears (Tears Naturale II, Alcon) are prescribed as needed. Patients are seen on the first and third postoperative days. On the third day, the contact is removed if the cornea has re-epithelialized; if re-epithelialization is incomplete, patients return on the fifth post-operative day for contact removal. Patients were evaluated at one, two, three, and six months. The results were analyzed using the Simstat 3.5 statistical program.

Results

The mean pre-operative sphere value was −6.8 D for 315 eyes. Of this number, 167 were categorized as low myopic: between −1 and −6 D, with a mean sphere equal to 4.48 D (S.D.±1.23 D); 106 were moderately myopic: between −6 and −10 D, with a mean sphere of −7.65 D (S.D. ±1.05); and 42 were considered highly myopic: between −10 D to −27 D, with a mean sphere of −13.97 D (S.D.±3.61 D). (see Tables 3,4,5,6) Astigmatism greater than −0.5 D was present in 185 of these eyes, with a mean value of −1.16 D±0.76 (range −0.75 D to −4.75 D).

At one month post-operative, the majority of eyes were slightly hyperopic, with a mean of +0.81 D±0.86 D for the whole population. This regressed to a mean of −0.11 D±1.16 D by the sixth month. (see Table 3: Mean Sphere Values).

TABLE 3

Mean sphere values for all degrees of myopia before and after MP-PRK

| Sphere | Mean Value | No. of Eyes |
| --- | --- | --- |
| Before | −6.8 ± 3.6 | 315 |
| 1 Month | 0.81 ± 0.86 | 271 |
| 2 Months | 0.3 ± 0.77 | 208 |
| 3 Months | 0.15 ± 0.78 | 199 |
| 6 Months | −0.11 ± 1.16 | 92 |

The variation for each of the groups is shown in Table 4 (Mean Sphere Values—Low myopia), Table 5 (Moderate myopia) and Table 6 (High myopia).

TABLE 4

Mean sphere values in the low myopia group before and after MP-PRK

| Sphere | Mean Value | No. of Eyes |
| --- | --- | --- |
| Before | −4.48 ± 1.23 | 167 |
| 1 Month | 0.54 ± 0.63 | 146 |
| 2 Months | 0.15 ± 0.48 | 113 |
| 3 Months | 0.06 ± 0.45 | 104 |
| 6 Months | 0.02 ± 0.59 | 38 |

TABLE 5

Mean sphere values in the moderate myopia group before and after MP-PRK

| Sphere | Mean Value | No. of Eyes |
| --- | --- | --- |
| Before | −7.65 ± 1.05 | 106 |
| 1 Month | 1.03 ± 0.77 | 90 |
| 2 Months | 0.48 ± 0.62 | 69 |
| 3 Months | 0.3 ± 0.64 | 67 |
| 6 Months | 0.02 ± 0.66 | 33 |

TABLE 6

Mean sphere values in the high myopia group before and after MP-PRK

| Sphere | Mean Value | No. of Eyes |
| --- | --- | --- |
| Before | −13.97 ± 3.61 | 42 |
| 1 Month | 1.41 ± 1.37 | 35 |
| 2 Months | 0.5 ± 1.63 | 26 |
| 3 Months | 0.13 ± 1.62 | 28 |
| 6 Months | 0.46 ± 2.16 | 21 |

Figure 1:
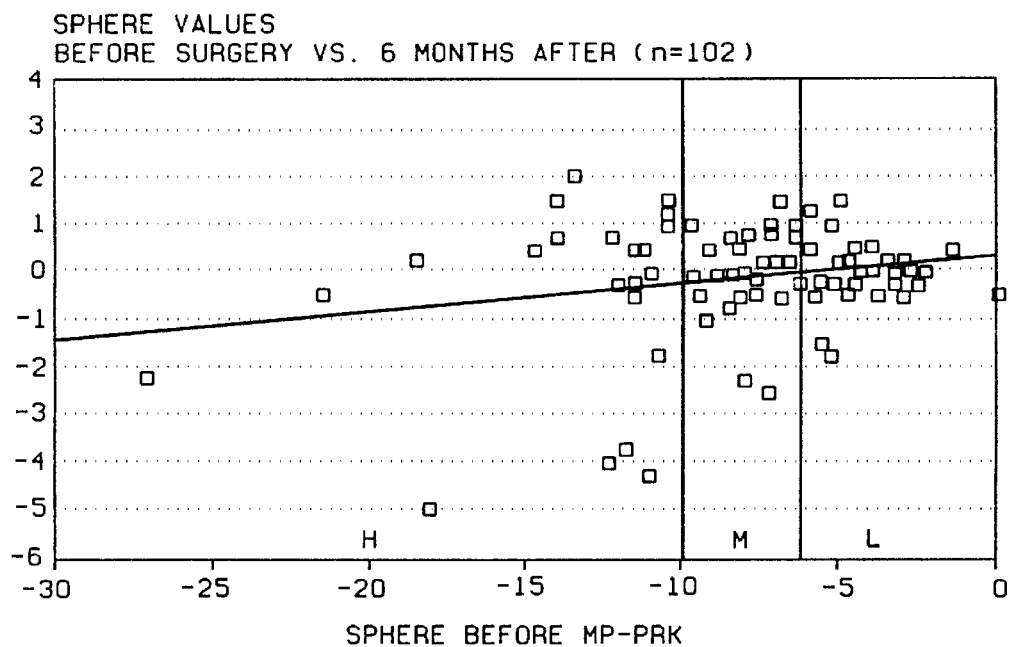
FIG. 1 is a scatter plot showing the sphere values obtained six months after MP-PRK against the pre-surgery sphere values.

At six months post-operative, the three groups have a mean sphere value very close to emmetropia. The low and moderate myopes have a relatively small standard deviation, while the highly myopic eyes have a larger variation (±−216); 89.4% of the low myopes, 97% of the moderate myopes, and 47.6% of the high myopes are within 1 D of emmetropia at six months; 76.2% of highly myopic eyes are within ±2 D of the intended correction. A scatter plot shows the sphere values obtained six months after MP-PRK versus the sphere before surgery (FIG. 1).

One hundred percent of low myopes, 99% of moderate myopes, and 84.6% of high myopes had a BCVA of 20/40 prior to PRK; 96.4% of low, 88.7% of moderate, and 38.5% of highly myopic eyes were 20/25 or bette, as shown in Tables 7,8, and 9.

TABLE 7

Percentage of eyes with best corrected visual acuity and uncorrected visual acuity in the low myopia group before and after MP-PRK

| | BCVA 20/40 and better | BCVA 20/25 and better | UCVA 20/40 and better | UCVA 20/25 and better |
| --- | --- | --- | --- | --- |
| Before | 100 | 96.4 | | |
| 1 Month | 100 | 94.5 | 98.6 | 82.0 |
| 2 Months | 100 | 98.2 | 99.0 | 95.2 |
| 3 Months | 100 | 98.1 | 99.0 | 94.9 |
| 6 Months | 100 | 97.4 | 94.6 | 89.2 |

TABLE 8

Percentage of eyes with best corrected visual acuity and uncorrected visual acuity in the moderate myopia group before and after MP-PRK

| | BCVA 20/40 and better | BCVA 20/25 and better | UCVA 20/40 and better | UCVA 20/25 and better |
| --- | --- | --- | --- | --- |
| Before | 99.0 | 88.7 | | |
| 1 Month | 98.9 | 85.7 | 92.1 | 59.6 |
| 2 Months | 100 | 97.1 | 96.9 | 81.5 |
| 3 Months | 98.5 | 98.5 | 96.9 | 87.7 |
| 6 Months | 100 | 96.9 | 93.5 | 80.6 |

TABLE 9

Percentage of eyes with best corrected visual acuity and uncorrected visual acuity in the high myopia group before and after MP-PRK

|  | BCVA 20/40 and better | BCVA 20/25 and better | UCVA 20/40 and better | UCVA 20/25 and better |
|---|---|---|---|---|
| Before | 84.6 | 38.5 | | |
| 1 Month | 74.3 | 31.4 | 51.5 | 12.1 |
| 2 Months | 73.1 | 42.3 | 66.7 | 12.5 |
| 3 Months | 75.0 | 50.0 | 68.0 | 32.0 |
| 6 Months | 85.7 | 52.4 | 63.2 | 26.3 |

Best corrected visual acuity in low myopia (Table 7) did not change significantly throughout the six-month follow-up: 100% of eyes remained at 20/40. At one month, 94.5% of low myopes saw 20/25 or better, at six months that number rose to 97.4%.

In moderate myopia (Table 8), the number of eyes that saw 20/40 and better stayed the same from the first through the sixth month (98.9% to 100%). However, the percentage of those seeing 20/25 increased from 85.7% at the first month visit to 96.9% six months post-operatively. In the high myopia group (Table 9), there was a decrease in the percentage of those seeing 20/40 or better during the first three months (73.1% to 75%). At the six-month visit, however, it returned to the preoperative value (85.7%). The percentage of those seeing 20/25 or better increased dramatically starting at the second-month post-operative visit with 42.3% to 52.4% at six months.

The percentage of eyes that had UCVA of 20/25 increased during the two months following the first month exam in all groups (Tables 7,8,9). At three months, 94.9% of low myopia, 87.7% of moderate, and 32% of high myopia were 20/25 and better. At six months, we found a small regression in the three groups: 89.2%, 80% and 26.3%.

Figure 4:
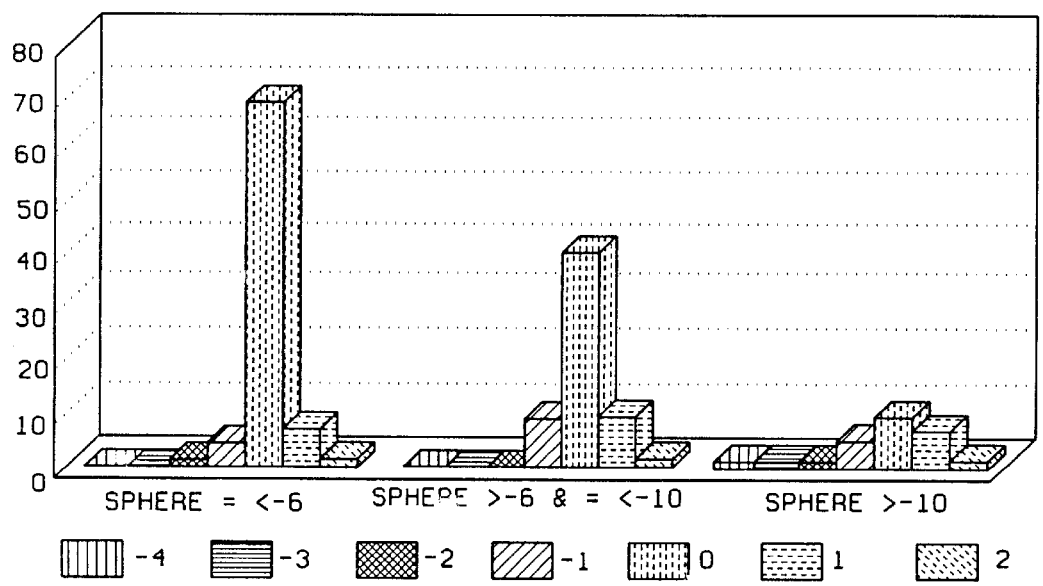
FIG. 4 is a chart showing the change in visual acuity for the three groups tested.

At one month, LBCVA had a mean value loss of 0.3 Snellen line, with 7.8% losing more than one line. At six months, the mean value was a gain of 0.1 Snellen line. Two cases (2.6%) had a loss of more than one line: one was due to macular bleeding, the other was due to +2 haze. FIG. 4 shows the change in visual acuity at three months for each group.

Figure 2:
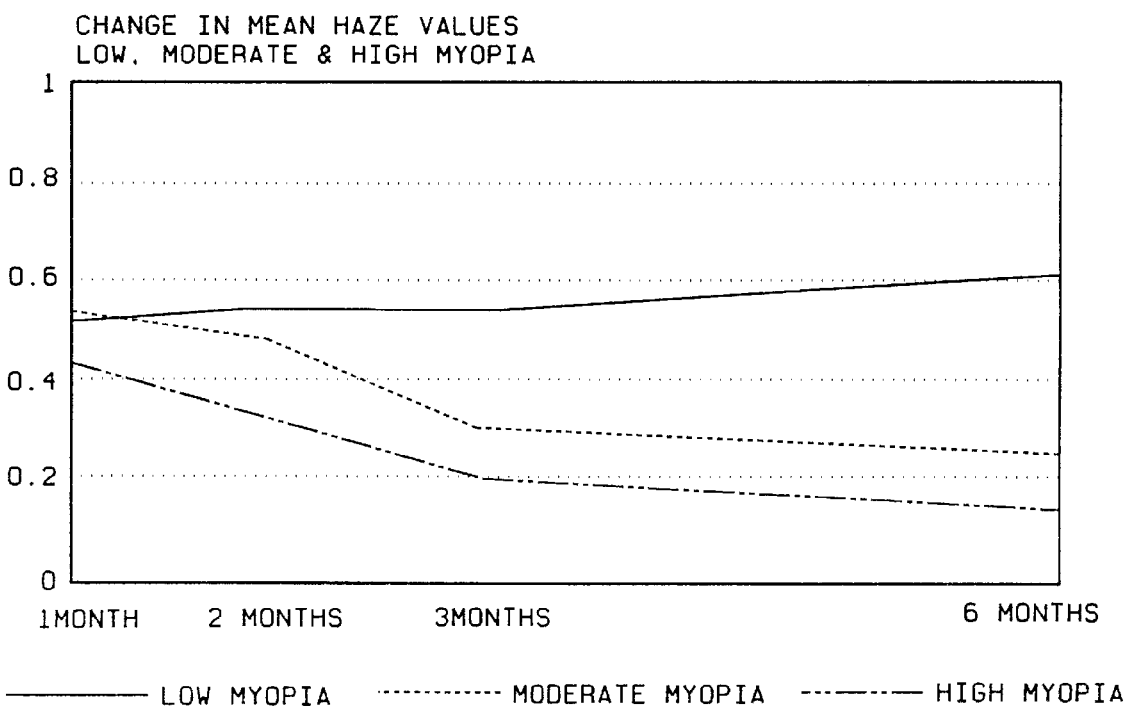
FIG. 2 is a chart showing the rate in decrease of haze values after MP-PRK.
Figure 3:
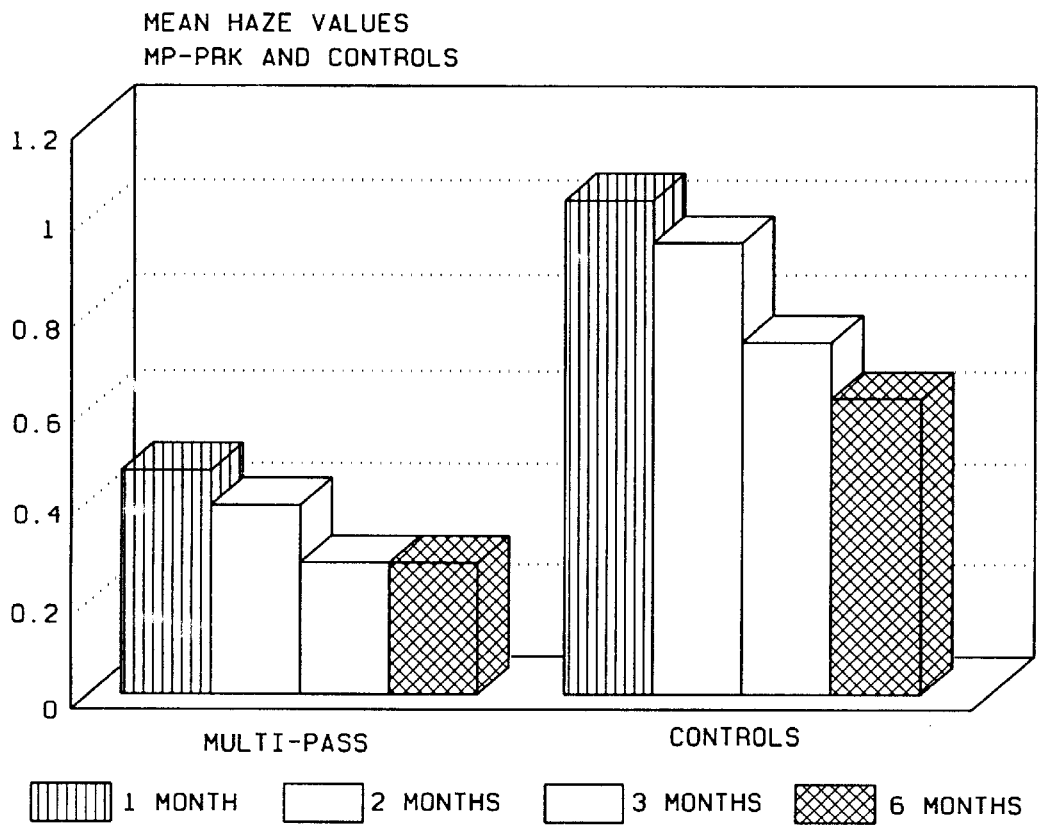
FIG. 3 is a chart comparing mean haze values against a control group.

Haze has always been a challenge to PRK. My approach tries to minimize this factor. The mean haze value was 0.47 (±0.39) one month after MP-PRK. There was no significant difference in haze intensity among the three groups: 0.43 for low myopia; 0.54 for moderate myopia; and 0.52 for high myopia. The only difference detected was in the rate of decrease in haze values at six months: 0.14 in low myopia; 0.25 in moderate myopia; and 0.61 in high myopia (see FIG. 2). Compared with a group of 138 eyes treated with the same lasers without using the multipass technique (the Central group), the haze value was significantly higher at 1.05 at one month and 0.65 at six months (FIG. 3). Only one eye at one month and one eye at six months had a haze value of 2.

TABLE 10

Degrees of quality of corneal topographies following MP-PRK expressed in percentage

| Month | No. of eyes | Good or fair | Wave | Central island |
|---|---|---|---|---|
| 1 | 257 | 67.7 | 30.4 | 1.9 |
| 2 | 185 | 70.8 | 28.1 | 1.1 |
| 3 | 188 | 78.7 | 20.7 | 0.5 |
| 6 | 82 | 82.9 | 15.9 | 1.2 |

The appearance of central islands in the ablation zone is one of the major reasons for poor quality of vision post-PRK. Table 11 shows corneal topography analysis following MP-PRK. A good result is defined as a smooth concave ablation area; fair is defined as a bulge of less than 0.05 D.

TABLE 11

Percentages of eyes in different ranges of the intended correction at 6 months following MP-PRK

| Groups | ±2D | ±1D | ±0.5D | No. of eyes |
|---|---|---|---|---|
| Low myopia | 100 | 89.4 | 86.8 | 38 |
| Moderate Myopia | 97.0 | 97.0 | 72.7 | 33 |
| High myopia | 76.2 | 47.6 | 33.3 | 21 |

A topographic wave is defined as a deformation that does not exceed 1.50 D, and an island is defined as any bulge greater than 1.50 D. At one month, 67.7% of topographies were considered good to fair; islands were seen in 1.9%. At six months, 82.9% were considered good to fair; islands were seen in 1.2%. The only significant difference between the results obtained with the two lasers was in topography. Less islands and waves were seen in eyes which had MP-PRK with the pre-treatment software.

Discussion

Fairly early in the history of PRK, regression due to haze or to other biological factors was considered a major complication of the technique. The majority of researchers believed that two methods could minimize regression: one method relied more heavily on drugs, primarily to regulate corneal healing. This was beneficial during the first few post-operative months, but it also produced undesirable side effects such as ocular hypertension or cataract. The second approach limited the depth of the ablation. Some investigators, faced with these seemingly insurmountable adverse effects, proposed other techniques such as keratomileusis, automated lamellar keratectomy (ALK) and laser in-situ keratomileusis (LASIK) as more effective procedures for correcting high myopia.

The high rate of complications and poor visual outcomes in treating high myopes instilled in researchers the belief that good results in PRK could be reliably obtained only for myopia of −6 D or less. Based on research, I questioned whether this −6 D ceiling is, in fact, a true obstacle to good, stable correction. Therefore, I decided to investigate new techniques that challenge this concept.

Photorefractive keratectomy is a less invasive approach compared to other surgical methods for correcting refractive errors. Outcomes for incisional procedures such as radial keratotomy, astigmatic keratotomy, ALK, and LASIK depend on the surgeon's skill and experience far more than in PRK. Moreover, ALK and LASIK remain unreliable in achieving the intended correction. It has been reported that these techniques often cause induced regular or irregular astigmatism, a complication that very rarely occurs in standard PRK procedures. Avoiding iatrogenic astigmatism is also important if retreatment is necessary: good results are obtained with greater consistency and ease in eyes that have no or minimal astigmatism. My results confirm that astigmatism is not induced with MP-PRK: in the group of 135 eyes technically without astigmatism (≦−0.50 D), there was no significant difference between the cylinder value before surgery and six months post-operative (−0.01±0.05, 0.18+−0.34). Five eyes had 0.50 to 1.25 D increase in cylinder; topographic analysis suggests that pre-operative astigmatism, undetectable by refraction, accounted for some of these results. The mean cylinder value six months post-operative was −0.34 D in 185 astigmatic eyes. No case had increased astigmatism.

The smoothness of the cornea is another major factor that promotes good healing after PRK. This is confirmed by research in animal models. Electron microscopy showed that nitrogen blown over rabbit corneas during PRK resulted in a rougher corneal surface than when nitrogen was not used, according to researchers. Much higher degrees of haze were also associated with nitrogen use. It has been found that a correlation exists between the presence of haze and the amount of regression in terms of the intended correction. It also has been found a relationship exists between haze and the re-establishment of the epithelial cell layer. Decreasing the haze formation, therefore, should result in more patients achieving intended correction.

I have tried to evaluate results from different centers that perform PRK. Exact comparisons are impossible, however, because different criteria were used to divide the myopic population into subgroups. I define high myopia as −10 D and above; in some centers high myopia is defined as −6 D and higher; in others it is defined as −8 D and above.

A recent article on high myopia reviewed the results of different research centers and specifically mentions the wide variation in results among these centers as noteworthy: 43% to 84% of eyes were within 2 D of the intended correction. In my group of high myopes, 76% were within 2 D and 48% were within 1 D of the intended correction, using the more stringent definition of high myopia. (Table 11)

No change in mean BCVA at six months in those seeing 20/40 or better, and the 14% increase in those seeing 20/25 BCVA lead us to believe that MP-PRK has no adverse effect on the cornea. The very low haze values associated with MP-PRK suggest that there are no contra-indications for retreatment. Because the second treatment is equivalent to a primary low myopia correction (our highest regression was −4.00 D six months post-operative), retreatment should not significantly increase any undesirable effects of PRK. Very preliminary results on retreatment tend to confirm this hypothesis.

After primary MP-PRK, high myopia decreases to −0.46 D±2.16 D at six months. The patient can then choose corrective glasses, contact lenses, or retreatment for residual myopia or hyperopia. The excimer laser is used for residual myopia; to date, the holmium laser remains a more appropriate solution for hyperopia.

The response in the moderate myopia group parallels that of the low myopes. Their BCVAs are 20/40 and 20/25 and their UCVA is 20/40, similar in both groups at six months. The only difference is seen in UCVA of 20/25 or better which is lower for moderate myopia (80.6% to 89.2%). Interestingly, their difference in BCVA of 20/25 before PRK is in the same range (88.7 to 96.4%), suggesting that MP-PRK does not adversely affect the visual acuity in low and moderate myopia.

None of the moderate myopic eyes have lost more than one Snellen line at three months; their mean response is no loss in visual acuity, with an equal number of patients losing or gaining one Snellen line. Ninety-eight percent of low myopic eyes and 93% of moderately myopic eyes are within 1 D of the intended correction at three months. This indicates that very few low myopes will require retreatment and that the number of retreatments for myopes between −6 and −10 D will also be low. There is more variation in the corrected sphere in moderate than in low myopia, but the difference is very small when the standard deviation of sphere at three months is compared: ±0.45 for low; and ±0.66 for moderate myopia. Finally, haze at one month is not different between the two groups, and the rate of resolution is only slightly slower in moderate myopia than in low myopia. Moderate myopia can be effectively corrected by using MP-PRK with an outcome that is very similar to the results achieved in the low myopia group. The only difference is in the greater variation in the corrections, thereby resulting in a potentially larger number of retreatments.

Corneal topographies obtained during follow-up provide the first clue as to the quality of the ablation. Many researchers have complained about the high percentage of central islands, well recognized as a predictor of poor visual outcome. Any corneal deformation correlates with poor vision, and, if persistent becomes an important factor in the decision to retreat. Pre-treatment in the central portion of the ablation was proposed to decrease the incidence of central islands. Our results show that MP-PRK appears to be another effective technique. Central islands were present in only five eyes during the first month post-operative. At six months, only one eye was effected.

Interestingly, central islands appeared almost entirely in the low myopia group who were treated with the laser which do not integrate a pre-treatment protocol. There was only one exception, a highly myopic eye with a transient island which appeared two months post-operative, probably due to epithelial hyperplasia.

The number of passes also has a positive influence on final results Islands that appear after one-pass PRK are probably due to an uneven central ablation. With more passes, the central zone receives a larger amount of laser energy, and therefore ablates more evenly. Another explanation for the creation of central islands is related to the pooling of fluid on the cornea generated during ablation: it is possible that this fluid evaporates during the interval between two passes, thereby allowing the laser beam more direct access to the cornea. Because no islands appeared in the group who had pretreatment, we have decided to systematically incorporate a pretreatment protocol for the laser without pretreatment software.

Another advantage in using the MP-PRK is its ability to produce a better centration. Some authors have noted failure to achieve the attempted refractive result when the treatment was decentered. With MP-PRK, the beam is recentered between each pass, not only when the surgeon detects eye movement.

I have not conducted an histologic analysis of the corneas to assess that MP-PRK does, in fact, produce smoother corneal surfaces. The significant decrease in hazing associated with MP-PRK indicates that the cornea remains in a more physiologic state with this technique than in other PRK techniques. Studies should be performed in the near future to verify this hypothesis.

I believe the incorporation of the algorithms investigated in this study into manufacturer-provided software will not only simplify treatment, but allow for greater reproducibility. It is also possible that the MP-PRK technique may create smoother ablations when used in other excimer laser systems designed for the treatment of myopia and astigmatism. The name for the algorithms would be Multizone/Multipass Algorithms.

I claim:

1. A method of performing photorefractive keratectomy with a surgical laser on a cornea of an eye to correct a refractive error of the cornea, the method comprising:

performing a preoperative topographic analysis of the cornea of the eye;

anesthetizing the eye;

removing a corneal epithelium; and performing corneal ablations of the cornea with the surgical laser using multiple passes in multiple zones, the corneal ablations being made from an inner zone to an outer zone of varying ablative depth, the width of each respective zone being varied to an irregular dimension with respect to other zones, each corneal ablation being titrated to the refractive error of the cornea based upon a predetermined algorithm, and the surgical laser being re-centered between each of the multiple passes.

2. The method of claim 1 including a final step of performing a follow-up corneal tophographical analysis.

3. A method of performing photorefractive keratectomy with a surgical laser on a cornea of an eye to correct a refractive error of the cornea, the method comprising:

performing a preoperative topographic analysis of at least a portion of the eye;

anesthetizing the eye;

removing a corneal epithelium;

centering the surgical laser;

performing a pretreatment ablation of the cornea with the surgical laser;

re-centering the surgical laser;

performing a first refractive correction on the cornea;

re-centering the surgical laser; and performing a second refractive correction on the cornea;

wherein each of the first refractive correction and the second refractive correction is titrated to the refractive error of the cornea based on a predetermined algorithm for a known dioptric correction.

4. The method of claim 3 including a final step of performing a follow-up corneal tophographical analysis.

5. A method of performing photorefractive keratectomy with a surgical laser on the cornea of an eye to correct a refractive error of the cornea, the method comprising:

performing a preoperative topographic analysis of the cornea of the eye;

anesthetizing the eye;

removing a corneal epithelium; and performing a plurality of passes of corneal ablation in a plurality of zones with the surgical laser, the width of each zone being varied to an irregular dimension with respect to other zones, each ablation being titrated to the refractive error of the cornea based on a predetermined algorithm for a known dioptric correction, the surgical laser being re-centered between each of the plurality of passes.

6. The method of claim 5 including a final step of performing a follow-up corneal tophographical analysis.

7. A method of performing corneal ablation, the method comprising:

performing a first pass corneal ablation of a plurality of zones of a cornea with a surgical laser;

re-centering the surgical laser; and performing a second pass corneal ablation of the plurality of zones of the cornea with the surgical laser;

wherein the width of each zone of said plurality of zones is varied to an irregular dimension with repect to other zones.

8. The method of performing corneal ablation according to claim 7, wherein:

the corneal ablations are made from an inner one of the plurality of zones to an outer one of the plurality of zones.

9. The method of performing corneal ablation according to claim 8, wherein:

each corneal ablation is titrated to a refractive error of the cornea based upon a predetermined algorithm.

10. The method of performing a corneal ablation according to claim 7, further comprising, before performing the first pass corneal ablation:

centering the surgical laser.

11. A method of performing corneal ablation, the method comprising:

firstly centering the surgical laser;

performing a first refractive correction on the cornea;

secondly centering the surgical laser; and performing a second refractive correction on the cornea.

12. The method of performing corneal ablation according to claim 11, wherein:

one of the first refractive correction and the second refractive correction corrects an astigmatism condition of the cornea; and the other of the first refractive correction and the second refractive correction corrects one of a myopic and hyperopic condition of the cornea.

13. The method of performing corneal ablation according to claim 12, wherein:

each of the first refractive correction and the second refractive correction is titrated to a refractive error of the cornea.

14. The method of performing corneal ablation according to claim 11, wherein:

the first refractive correction is performed across a plurality of zones before the secondly centering of the surgical laser.

15. The method of performing corneal ablation according to claim 13, wherein:

each of the first refractive correction and the second refractive correction is titrated to the refractive error of the cornea based on a predetermined algorithm for a known dioptric correction.

16. The method of performing a corneal ablation according to claim 11, further comprising, before the firstly centering of the surgical laser:

initially centering the surgical laser; and performing a pretreatment ablation of the cornea.

* * * * *